United States Patent [19]

Vieth et al.

[11] 3,977,941

[45] *Aug. 31, 1976

[54] PROTEIN-ENZYME COMPLEX MEMBRANES

[75] Inventors: Wolf R. Vieth, Belle Mead; Shaw S. Wang, North Brunswick; Seymour G. Gilbert, Piscataway, all of N.J.

[73] Assignee: Research Corporation, New York, N.Y.

[ * ] Notice: The portion of the term of this patent subsequent to Oct. 22, 1991, has been disclaimed.

[22] Filed: Feb. 4, 1974

[21] Appl. No.: 439,110

Related U.S. Application Data

[62] Division of Ser. No. 135,753, April 20, 1971, Pat. No. 3,843,446.

[52] U.S. Cl. .................................... 195/63; 195/68; 195/DIG. 11

[51] Int. Cl.[2] .................................... C07G 7/02

[58] Field of Search ................ 195/63, 68, DIG. 11; 106/161

[56] References Cited

UNITED STATES PATENTS

| | | | |
|---|---|---|---|
| 2,920,000 | 1/1960 | Hochstadt et al. | 106/161 |
| 3,705,084 | 12/1972 | Reynolds | 195/63 |

OTHER PUBLICATIONS

Silman, et al., Some Water-Insoluble Papain Derivatives, Biopolymers, vol. 4, 1966 (pp. 441-448).

Goldman, et al., Papain Membrane on a Collodion Matrix: Preparation and Enzymic Behavior, Science vol. 150, 1965 (pp. 758-760).

*Primary Examiner*—David M. Naff
*Attorney, Agent, or Firm*—Oblon, Fisher, Spivak, McClelland & Maier

[57] ABSTRACT

Enzymatically active protein-enzyme complex membranes are prepared by treating a swollen protein membrane with an aqueous solution of a compatible active enzyme. These membranes are used to effect enzymatic reactions.

10 Claims, No Drawings

PROTEIN-ENZYME COMPLEX MEMBRANES

This is a division of application Ser. No. 135,753 filed Apr. 20, 1971, now U.S. Pat. No. 3,843,446.

BACKGROUND OF THE INVENTION

1. Field Of The Invention

This invention relates to protein-enzyme complexes in membrane form and more particularly to enzymatically active protein-enzyme complex membranes which can be used for catalyzing enzymatic reactions. In another aspect, this invention relates to methods for preparing said enzymatically active membranes and to methods of using said enzymatically active membranes.

2. Description Of The Prior Art

Enzymes are protein catalysts which have been used for a wide variety of industrial and research applications, particularly in pharmaceuticals, paper and textile processing, etc. They are highly specific in their activity and generally do not generate significant quantities of undesirable byproducts. Enzyme reactions are industrially advantageous since they do not require a large investment in heat transfer equipment and can be easily staged, thereby minimizing the problems associated with interstage product separations.

One problem which has long concerned those dealing with industrial applications of enzymes, however, is the difficulty in separating or recovering enzyme materials. In most commerical processes, the enzymatic reaction is effected by simply admixing the enzyme with the substrate, and thereafter inactivating and/or recovering the enzyme from the products or the unreacted substrate following the reaction. This procedure, however, has frequently resulted in damage to the product and inherent loss of large quantities of enzyme, since usually no enzyme is recovered or, if attempted, the yields are quite low.

Another problem which has been of significant concern to those engaged in this technology, is that the enzymes usually are used in an aqueous dispersion form. As a rule, however, enzymes in this form have a limited shelf life and, especially, if stored in dilute form, will undergo rapid loss of activity upon storage.

To alleviate these problems, the art has developed various so-called "immobilized enzymes" in which the enzymes are immobilized or bound to inert or insoluble carriers. At the completion of the enzymatic reaction, these insoluble enzyme-containing materials can be separated from the unreacted substrate or product by techniques such as ultrafiltration or the like.

The selection of a suitable inert carrier, however, has been quite difficult, since the carrier must not only be inert to the enzyme, but it must not inhibit the catalytic activity of the enzyme, nor cause undesirable unspecific absorption. Moreover, the carrier should present a minimum of steric hindrance toward the enzyme-substrate reaction. A wide variety of prior art carriers have been proposed, depending upon the particular type of enzyme used and the particular enzymatic reaction desired. For instance, among those prior art carriers disclosed in the open literature include, synthetic polymers such as polyamides, cellulose derivatives, various clays, and ion-exchange resins, particularly DEAE-cellulose, and DEAE-dextrans, as discussed in Suzuki, et al., *Agr. Biol. Chem.*, Volume 30, No. 8, Pages 807–812 (1966). Prior art methods of preparing imobilized enzymes have included direct covalent bonding, indirect bonding through an intermediate compound, cross-linking of the enzyme or trapping the enzyme in polymer lattices.

None of these prior art techniques or carriers, however, have been entirely satisfactory for all purposes. Synthetic polymer carriers are expensive and frequently are not readily available. Moreover, they often require special treatment in order to chemically bind the enzyme to the carrier. The cellulose derivatives are generally unsuitable as binders for carbohydrases, since carbonhydrates are substrates for these enzymes. Ion-exchange resins, such as DEAE-cellulose and DEAE-dextran, have ion-exchange properties, which may not be desirable for certain applications. The problem of enzyme liberation from a carrier is one weak point in many immobilized enzyme preparations, and is particularly troublesome in the case of amylase bound to acid clay, which becomes liberated during the hydrolytic reaction of starch.

One particular disadvantage of the prior art methods of immobilizing enzymes is that they have resulted in the formation of insoluble pastes, particles or granular materials. While such forms are suitable, and even possibly desirable for certain applications, for other applications, these forms impose severe limitations, especially when they are used for large-scale or long-term continuous processes.

A need exists, therefore, for aan enzyme carrier which can be formed into a variety of shapes and hence can be used as a structural part of a reaction system, so as to eliminate entirely separation problems. More specifically, a need exists for a membrane or film-like carrier which is capable of complexing and binding enzymes thereto without hindering their catalytic activity, so that enzymatic reactions can be effected merely by passing the substrate over the active membrane or film. The present invention fills such a need.

SUMMARY OF THE INVENTION

Accordingly, one object of this invention is to provide immobilized enzymes in membrane form.

Another object of this invention is to provide a technique for producing immobilized enzymes in membrane form.

A still further object of this invention is to provide a technique for effecting enzymatic reactions by passing an enzymatically active substrate over an enzyme-carrier complex membrane, which is characterized by good catalytic activity.

Briefly, these and other objects have now been attained in one aspect of this invention by immobilizing enzymes on protein membranes.

Suitable membranes include both synthetic poypeptides and natural protein, in unmodified or modified forms. Enzyme immobilization is accomplished in one case by swelling a protein membrane, and thereafter soaking said membrane in an aqueous dispersion of an enzyme for a period of time sufficient to complex the enzyme with the protein.

The complexing mechanism between enzymes and protein membranes or film-like protein carriers involves the formation of multiple hydrogen bonds, salt linkages, and van der Waals interactions. Complex formation is facilitated at a pH between the isoelectric points of the enzyme and the protein membrane.

DESCRIPTION OF THE PREFERRED EMBODIMENTS

A wide variety of synthetic polypeptides and natural proteins may be used in the present invention. Non-limiting example of suitable natural proteins include collagen, zein, casein, ovalbumin, wheat gluten, fibrinogen, myosin, mucoprotein, and the like. Non-limiting examples of suitable synthetic polypeptides include polyglutamate, polyaspartate, polyphenylalanine, polytyrosine, and copolymers of leucine with p-amino phenylanaline.

The selection of a particular synthetic polypeptide or natural protein, in modified or unmodified form, will be largely determined by the nature of the enzyme being complexed, the substrate to be treated, and the reaction environment to be encountered. Because inertness their interness to a large number of enzymes, collagen and zein are preferred natural protein materials. While the following description of this invention illustrates the use of collagen and zein, it will be apparent that the invention is equally applicable, with obvious modifications, to other membranes of the aforementioned types. In one embodiment, a collagen film is prepared by casting a dispersion of collagen according to state of the art techniques. The film is then swollen, washed in water and soaked in an enzyme solution. After refrigerated storage to allow diffusion of the enzyme into the collagen, the film may be layered on a base, such as a cellulose acetate film, and dried.

Collagen is a hydroxyproline, glycine-type protein, which is the chief organic constituent of connective animal tissue and bones. Chemically, collagen is distinguishable from other proteins by its unusually high glycine content, which accounts for approximately one-third of the amino acid residues therein; the high content is proline and hydroxyproline; the presence of hydroxyglycine, which is unique among proteins; and in having notably small amounts of aromatic and sulfur-containing amino acids. It can be obtained in good yields from a wide variety of mammal and fish parts, and is frequently obtained from pork, sheep and beef tendons; pigskins; tanner's stock, which are calfskins not usable for leather; and ossein, which is tissue obtained by drying cattle bones remaining after acid treatment to remove calcium phosphate.

One suitable method for forming a collagen membrane is as follows: The collagen source is first treated with an enzyme solution to dissolve the elastin which encircles and binds the collagen fibers. Proteolytic enzymes, from either plant or animal sources, may be used for this purpose. although other types of anzymes are equally satisfactory. The collagen source is then washed with water and the soluble proteins are lipids are removed by treatment with a dilute aqueous solution of a chelating agent, such as ethylene diamine tetrasodium tetraacetate. The collagen fibers are then swollen in a suitable acid, such as cyanoacetic acid, as described in Hochstadt, et al., U.S. Pat. No. 2,920,000, so as to form a collagen fiber dispersion. This dispersion can then be extruded or cast into a suitable membrane form. The dried collagen membrane is then annealed at 60°C., 95% R. H. for 48 hours. The said collagen fiber dispersion can also be electrodeposited according to British Pat. No. 1,153,551 to form suitable membranes.

Of course, any one of the many state of the art techniques can be used to form suitable collagen membranes, and the above descriptions are only exemplary of suitable prior art techniques.

The collagen membranes useful in the present invention generally have a thickness of from 0.005 mm to 0.1 mm. and preferably from 0.01 mm. to 0.05 mm. When the thickness is less than 0.05 mm., the membrane loses its desirable strength and may not form a completely integral film without pinholes or other structural defects.

When the thickness exceeds 0.1 mm., the cost of the complex increases without necessarily increasing the efficiency of the complex in its performance.

Other materials may be added to the membrane to accomplish specific aims. For example, plasticizers may be used to modify the molecular structure of the membrane to provide greater resilience by allowing for chain slippage. Humectants may maintain a more favorable water binding capacity. Cross-linking agents, heat annealing, or tanning with chrome or formaldehyde, as described in the prior art, may be employed to inhibit hydrolysis or to provide additional bonding sites for the desired enzyme, thereby enhancing enzyme retention.

The collagen membrane is then prepared for complexing with the enzyme, generally by being swollen with a low molecular weight organic acid, or in some instances with suitable bases so that the pH ranges from about 2–12. Since acids include lactic acid and cyanoacetic acid. If desired, plasticizers or other additives heretofore mentioned may be added during the swelling step. Swelling is accomplished by submerging the membrane in the acid bath for between ½ hour and 1 hour, depending upon the particular conditions of the bath, generally at room temperature in excess of this level will result in the conversion of the collagen to a soluble gelatin.

The membrane is swollen by the acidity of the organic acid added and the use of the acid as a plasticizer. No other additive is needed. A change in water binding capacity results from the acid treatment.

Following the swelling treatment, the swollen collagen membrane is washed thoroughly with water until the pH level of the membrane is within the acceptable range for the particular enzyme being complexed.

The swollen, washed membrane is then soaked in an aqueous enxyme-containing solution until complexing occurs. Usually, this requires a period of from 10 hours to 2 days. The temperature range during this time should be maintained within 4°C. to 20°C., depending upon the particular enzyme used. Maximum enzyne uptake is measured by activity after washing, and indicates when complexing is complete.

The enzyme-collagen complex medium should be carefully dried, preferably at about room temperature or below, so as not to damage the bond enzyme.

As a second example of using natural protein to complex enxymes, zein film is prepared by casting a solution of zein according to state of the art techniques. The same procedure was used to prepare protein-enzyme complexes as was done with collagen film, except that the swelling of the zein film was aided by adding plasticizers, such as 1.5-pentane-diol.

Zein is the prolamin (alcohol-soluble protein) of corn. It is the only commercially available prolamin and one of the few readily available plant proteins. Zein occurs primarily in the endosperm of the corn kernel. The amount of alcohol-soluble protein is directly related to the total endosperm protein content with zein contents ranging from 2.2 to 10.4% of the dry substance in various corn samples.

Zein is characterized by a relative deficiency of hydrophilic groups in comparison with most proteins. In fact, the high proportion of nonpolar (hydrocarbon) and acid amide side chains accounts for the solubility of zein in organic solvents and its classification as a prolamin.

One of the commercial zeins is Argo Zein G-200, manufactured by Corn Products Refining Company, Argo, Illinois. Films casting solutions can be formulated on a pure component basis, taking into account the water content of the raw zein and other reagents. The casting solutions are prepared by dissolving the protein in the organic solvent of choice by gentle stirring, at room temperature, for a period of 1–2 hours, during which period solution is complete. Examples of suitable solvents which may be employed include 81% (wt./wt.) isopropyl alcohol and 4% methyl cellosolve (ethylene glycol monoethly ether). The clear solutions, which contained 20 – 30% by weight of dry zein, are of amber color. Curing agents, such as formaldehyde, and a plasticizer may be added shortly before film casting.

Of course, any one of the many state of the art techniques can be used to form suitable zein membranes, and the above description is only exemplary of one suitable prior art technique.

The zein membranes useful in the present invention generally have a thickness of from 0.005 mm. to 0.1 mm. The zein membrane is then prepared for complexing with the enzyme by swelling with a plasticizer, if plasticizer was not added before film casting. Suitable plasticizers include 1.5-pentane-diol, glycerol, and sorbitol. This is accomplished by submerging the membrane in a bath of 2% (w/w) plasticizer in water for 10 hours at room temperature. The swollen membrane is then dried with tissue paper and soaked in an aqueous enzyme solution until complexing is completed. Usually, this requires a period of from 10 hours to 2 days. The temperature range during this period should be maintained within 4°C. to 20°C., depending upon the particular enzyme used.

The enzyme-zein complex medium should be carefully dried, preferably at about room temperature or below, so as not to damage the bound enzyme.

A wide variety of different types of enzymes can be complexed with natural proteins such as collagen, zein, and the like in this manner, depending upon the particular application intended. For instance, suitable enzymes include amylases, lysozyme, invertase, urease, celluloses, catecholmethyltransferase, sucrose 6-glucosyl-transferase, carboxyl esterase, aryl esterase, lipase, pectin esterase, glucoamylase, amylopectin-1,6-glucosidase, oligo-1,6-glucosidase, polygalacturonase, $\alpha$ -glucosidase, $\beta$ -glucosidase, $\beta$ -galactosidase, glucose oxidase, galactose oxidase, catechol oxidase, catalase, peroxidase, lipoxidase, glucose isomerase, pentosanases, cellobiase, xylose isomerase, sulphite oxidase, ethanolamine oxidase, penicillinase, carbonic anhydrase, gluconolactonase, 3 -keto steroid $\Delta$ dehydrogenase, 11-$\beta$ -hydroxylase, and amino acid acylases. Compatible combinations of enzymes, and multienzyme systems can also be complexed with the collagen in this manner.

Especially suitable, however, are lysozyne, invertase, urease and amylases. Lysozyme is widely used to hydrolyze microorganisms in pharmaceutical research, and in sewage treatment, either alone or in combination with other enzymes, and/or bacteria. One particularly important application for lysozyme-protein membrane complex is in the lysis of cells.

Invertase or $\beta$-D-fructofuranosidase is widely used in the food and beverage industries, as well as for analytical purposes. Invertase can be used to catalyse the hydrolysis of sucrose to glucose and fructose or invert sugar. Invertase is effective in the hydrolysis of $\beta$-D-frustofuranosyl linkages in sucrose, raffinose, gentianose, and methyl and $\beta$ -fructofructose. One particularly important application for an invertase-protein membrane complex is in the continuous hydrolysis of sucrose.

Urease is a highly specific enzyme which can catalyze the transformation of urea to ammonium carbonate, and is often used to determine the urea content in urine specimens. Because of its highly specific activity, one utility for the urease-protein complex membrane is in kidney machine applications. More particularly, urease-protein complex membranes can be used for repeated hydrolysis or urea, such as in the treatment of human wastes.

$\alpha$-amylase is referred to as the "liquifying enzyme" and is known to randomly hydrolyze starch, glycogen, and dextrans. $\beta$ -amylase can produce maltose from sugar, glycogen and dextran. Other suitable amylases include $\alpha$-glucosidase, amyloglucosidase, amylo-1, 6-$\alpha$glucosidase (debranching enxyme), oligo-1, 6-glucosidase (limit dextrinase), isomaltase, and isotriase. As used herein, the term "amylase" refers generically to one or more of these and other amylases. One particularly important application of the amylase-protein complex of the present invention if in the continuous passage of starch substrates over the enzymatically active membrane to effect continuous hydrolysis of starch.

Several enzymes can be simultaneously complexed with the protein membrane. For instance, it is quite desirable to complex $\alpha$ -amylase with other types of enzymes, since $\alpha$ -amylase is capable or randomly cleaving a starch molecule, so as to provide reactive sites for other more specific enzymes.

Immobilized complexes formed in this manner provide good enzymatic activity. When an enzymatically active substrate is contacted with such complexes, a constant amount of the enzyme remains bound to the carrier throughout the reaction period so that there is no necessity to provide a separate separation procedure, as in the prior art. Moreover, it has been found that the enzyme-protein complexes of the present invention are stable over long periods of storage and can be washed repeatedly without significant loss in enzymatic activity.

While not washing to be bound by any theory, it is believed that the complexing mechanism between protein membranes or film-like protein carriers and enzymes involves the formation of multiple hydrogen bonds, salt linkages and van der Waals interactions. Complex formation is facilitated at a pH between the isoelectric points of the enzyme and the protein membrane.

It should be clearly understand that the art of preparing the membranes from collagen films, of the type which are used herein for complexing with the various enzymes is a well developed art and a variety of state of the art techniques are available. For instance, the Hochstadt, U.S. Pat. No. 2,920,000, mentioned above, is merely representative of suitable techniques for preparing collagen type films and membranes.

Having now generally described the invention, a further understanding can be obtained by reference to the following Examples, which are presented for purposes of illustration only and are not intended to be limiting unless so specified.

EXAMPLE 1 (lysozyme)

This example demonstrates the formation and use of a lysozyme collagen membrane complex.

Once cc. of a l mil thick collagen film (post-heated at 55°C., 90% R. H. for 48 hours) was swollen in a lactic acid solution (pH = 3) and then washed in running tap water for 5 minutes. The washed film was then soaked in an enzyme solution of 250 mg. in lysozyme in 15 cc. of water, and storated at 2°C. for 14 hours. The soaked film was then layered on cellulose acetate, and dried at room temperature to yield a lysozyme-collagen membrane complex.

A solution of *Micrococcus lysodeictikus* (300 mg. of dried cells per liter) was used to assay the enzymatic activity of the complex by measuring the decrease in optical density at 450 mu of the bacterial solution. The dried membrane complex was first washed with 10 liters of running water and its initial enzymatic activity measured. This was determined on the basis of the decrease in optical density divided by the initial optical density after a reaction period of 30 minutes. The complex was washed with 2 liters of water between individual experiments. Initial activity was 0.538, corresponding to 53.8% of the cells being lysed. The second repetition gave an activity of 0.420. corresponding to 42% lysis; the third repretition gave an activity of 0.489, or 48.9% lysis; and the fourth experiment gave an activity of 0.533, or 53.3% lysis.

EXAMPLE 2 (invertase)

This example describes the preparation and use of an invertase-collagen complex. 1.5 cc. of a 1 mil thick collagen film (untanned and stored at room temperature for a least 2 months) was swollen in a lactic acid solution (pH = 3). The film was then washed in water for one-half hour, and the washed film was soaked in a solution of 140 mg. invertase in 10 cc. of water and stored in a refrigerator overnight. The soaked film was then layered on a cellulose acetate substrate, and dried at room temperature. The dried film, which is a collagen-invertase membrane complex, was used in the following experiment to hydrolyze sucrose.

400 cc. of 6% sucrose solution was used as a substrate in the enzyme assay. Enzymatic activity was followed polarimetrically in a recirculation reactor system. After the complex was assayed for its activity, it was washed with 2 liters of water, and the activity again measured. This process was repeated over 20 times, with total washings of over 40 liters. The enzymatic activity of the invertase-collagen complex decreased gradually after washing, finally reaching a stable limit which held constant for over 10 liters of washing. The total elapsed time at this stage was 13 days.

TABLE 1

| No. of Washings | % sucrose inverted in 30 minutes of reaction time 25°C. pH 5 – 6 |
|---|---|
| 1 | 50 |
| 5 | 40 |
| 10 | 38 |
| 15 | 30 |
| 20 | 28 |
| 25 | 26 |
| 30 | 25 |
| 35 | 25 |
| 40 | 24 |

The enzymatic activity of the invertase complex at the stable lower limit corresponds to a reaction rate of $1.73 \times 10^{-3}$ mole/liter/minute. Assigning the complex the same turnover number as the free enzyme (370 moles of sucrose per mole of enzyme per second), the reaction rate above corresponds to the activity of 21.4 mg. of invertase in 1 liter of a 6% sucrose solution. Since only 1.5 cc. of an invertase complex was used to hydrolyze 400 cc. of substrate, the amount of invertase bound to 1.5 cc. is calculated to be 8.56 mg., or 5.7 mg. of invertase per cc. of the complex.

This series of experiments was done over a period of 13 days. The complex was stored at 2°C. in 5 cc. of distilled water when not being used.

EXAMPLE 3 (urease)

This Example describes the preparation and use of unrease-collagen membranes. One cc. of a 1 mil thick collagen film (post heated at 60°C., 95% R. H. for 48 hours was swollen in lactic acid solution, pH—3, then washed in water for one-half hour. The washed film was then soaked in an enzyme solution of 200 mg. of urease in 15 cc. of water for 16 hours. The film was then layered on a cellulose acetate substrate, and dried at room temperature.

Prior to use, the membrane-urease complex was washed with 5 liters of water and stored at 2°C. for 5 days before testing for urease activity.

TABLE 2

Hydrolysis of Urea by Urease-Collagen Membrane Complex

| Day No. | Conc. of Urea Solution in Units of $3.3 \times 10^{-3}$ M (initial) | % of Urea Hydrolyzed in the Reaction Time Indicated | | pH of Urea Solution | |
|---|---|---|---|---|---|
| | | Through Potentiometric Measurement | Through Use of Nessler's Reagent | Initial | Final |
| [a]1 | 100 | 0.21% (30 min.) | — | — | — |
| 2 | 100 | 0.3% (20 hrs.) | — | — | — |
| 3 | 10 | 0.20% (160 min.) | — | — | — |
| 4 | 1 | 7.6% (200 min.) | — | — | — |
| [b]5 | 1 | [c]14% (20 min.) | — | — | — |
| 8 | 1 | 7.6% (20 min.) | 8% (20 min.) | — | — |
| 8 | 1 | 3.8% (20 min.) | 5% (20 min.) | 7.30 | 7.40 |

TABLE 2-continued

| Hydrolysis of Urea by Urease-Collagen Membrane Complex | | | | | |
|---|---|---|---|---|---|
| Day No. | Conc. of Urea Solution in Units of $3.3 \times 10^{-3}$ M (initial) | % of Urea Hydrolyzed in the Reaction Time Indicated: Through Potentiometric Measurement | % of Urea Hydrolyzed in the Reaction Time Indicated: Through Use of Nessler's Reagent | pH of Urea Solution: Initial | pH of Urea Solution: Final |
| 8 | 1 | 99% (20 hrs.) | 99% (20 hrs.) | 7.30 | 7.90 |

[a]One cc. membrane complex was used in all the experiments to hydrolyze 50 cc. urea solution.
[b]Membrane complex used on Day 4 was soaked in 50 cc. of enzyme solution (100 mg. urease/50 cc.) for 14 hours, and washed with 2 liters water before it was used on Day 5.
[c]Average of two experiments.

Urease activity was followed by direct potentiometric measurement of ammonium ion concentration through the use of a Beckman 39137 cationic sensitive electrode, and also measured colorimetrically with Nessler's reagent. Ammonium sulfate was used to obtain a standard curve in both cases. One drop of freshly prepared Nessler's reagent was added to 2 ml. of substrate solution, and the color intensity was measured spectrophotometrically at a wavelength of 430 m$\mu$. Three concentrations of urea, namely, $3.3 \times 10^{-1}$, $3.3 \times 10^{-2}$, and $3.3 \times 10^{-3}$ molar, in distilled water were used. Activity of the membrane complex was tested over a period of one week. When not in use, the complex was stored immersed in 50 cc. distilled water at room temperature. Results show that 99% hydrolysis of 50 ml. of a $3.3 \times 10^{-3}$ molar solution was obtained in 20 hours by using 1 cc. of the membrane complex, which had already been used for over 1 week.

EXAMPLE 4 (amylase)

This Example demonstrates the formation and use of an amylase-collagen membrane complex. Two cc. of a 1.5 mil thick collagen film (post-heated at 60°C., 95% R. H. for 48 hours) was swollen in a lactic acid solution for one-half hour at pH 3. The film was then washed in running tap water for 5 minutes, and the washed film then soaked in a solution of 200 mg. of malt amylase in 15 cc. of water, and stored at 2°C. for 15 hours. There was no necessity to remove excess enzyme solution, and the soaked film was immediately layered on a cellulose acetate film substrate 1 to 2 mils thick and dried at room temperature. The dried film, a collagen-amylase membrane complex, was used to hydrolyze starch. 50 cc. of a 1% starch solution was used as a substrate in the enzyme assay. Enzymatic activity was measured by the decrease in the blue color intensity of the starch-iodine complex (change in optical density at 400 m$\mu$.). A standard iodine reagent was prepared by dissolving 30 grams of potassium iodide and 3 grams $I_2$ in one liter of distilled water. One drop of this reagent was added to 20 cc. of the reacted substrate which had been incubated with 2 cc. of the amylase-collagen membrane complex at 40°C. for 15 minutes, and the absorption at 400 m$\mu$. was measured.

The following shows the results of starch hydrolysis by a collagen-amylase membrane complex which was washed with 10 liters of water prior to the experiment. After 15 minutes, the color of the iodinated starch solution changed from blue to violet, consistent with the degradation of the starch molecules from an initial average degree of polymerization in excess of 30 to a final average degree of polymerization of 10 to 15. Upon the first run, amylase activity of 2 cc. of film in 50 cc. of a 1% starch solution reacted for 15 minutes at 40°C. gave an amylase activity, as measured by the quotient of the decrease in optical density at 400 m$\mu$. divided by the initial optical density at 400 m$\mu$. of 0.700. The complex was washed with two liters of water, and the second run gave an amylase activity of 0.325. After an additional washing, an amylase activity of 0.500 was obtained for the third run.

EXAMPLE 5 (cellulase)

This Example describes the preparation and use of a cellulase-collagen complex. 1 cc. of a 1.5 mil thick collagen film (post-heated at 55°C. and 95% R. H. for 30 hours, and then stored at room temperature for 2 months) was swollen in a lactic acid solution (pH = 3). The swollen film was then washed in water for one-half hour, and the washed film was bathed in a solution of 200 mg. cellulase in 10 cc. of water and stored at 4°C. for 14 hours. The soaked film was then layered on a cellulose acetate substrate, and dried at room temperature. The dried film was washed in one liter of water for two weeks at 4°C. before it was used in the following experiment to hydrolyze carboxyl methyl cellulose (CMC). 50 cc. of 1.5% CMC was used as a substrate in the enzyme assay. Enzymatic activity was followed by monitoring the decrease in relative viscosity of the substrate, as measured by the Ostwald viscosimeter. Between runs, the film was washed with 2 liters of water. The results obtained are shown in Table 3.

TABLE 3

| No. of Run | Decrease in Relative Viscosity over a reaction Time of 30 min. at 20°C. |
|---|---|
| Control | 12.90 |
| 1 | 10.75 |
| 2 | 7.74 |
| 3 | 5.60 |
| 4 | 5.43 |
| 5 | 5.27 |

As shown in the above results, the cellulase-collagen complex was able to decrease the viscosity of the substrate to less than half of its initial value after five runs. During the fifth run, the relative viscosity of the substrate decreased to 1.43 after 18 hours of reaction time.

EXAMPLE 6 (invertase-zein)

This Example describes the preparation and use of an invertase-zein complex. 2 cc. of a 1.5 mil thick zein film (formaldehyde-tanned) was swollen in 2% (W/W) 1.5-pentanediol. The film was then dried with tissue paper, soaked in an enzyme solution of 200 mg. invertase in 15 cc. of water, and stored in a refrigerator overnight. The soaked film was then layered on a cellulose acetate substrate, and dried at room temperature. The dried film, which is a zein-invertase membrane complex, was used in the following experiment to hydrolyze sucrose.

400 cc. of 6% sucrose solution was used as a substrate in assaying enzyme activity which was followed polarimetrically in a recirculation reactor system, as in Example 2. After the complex was assayed for its activity, it was washed with 2 liters of water and reused. The results obtained are shown in Table 4.

TABLE 4

| No. of Washings | % Sucrose Inverted in 2 Hours of Reaction Time, at 25°C. and pH6 |
|---|---|
| 1 | 40 |
| 2 | 16 |
| 4 | 8 |
| 6 | 8 |
| 10 | 6 |
| 15 | 7 |

The enzymatic activity of the invertase-zein complex decreased gradually after washing, finally reaching a stable limit as did the collagen-invertase complex of Example 2.

EXAMPLE 7 (glucose isomerase)

This example demonstrates the formation and use of a glucose isomerase-collagen membrane complex.

One cc. of a 1 mil thick collagen film (post-heated at 60°C., 90% R. H. for 28 hours) was swollen in a lactic acid solution (pH=3) and then washed in running tap water for 5 minutes. The washed film was then soaked at 2°C. for 16 hours in 55 cc. of enzyme solution which had a total enzymatic activity of $5.4 \times 10^{-5}$ Unit (1 unit = 1 mole product formed/minute.)

The soaked film was then layered on cellulose acetate, and dried at room temperature to yield a glucose isomerase collagen membrane complex.

The membrane complex was used to catalyze the isomerization of D-glucose in 50 ml of a 9% solution buffered at pH 7.2, at 60°C. After a reaction time of two hours, 1 ml of the reaction solution was sampled and D-fructose formed was determined by the cysteine-carbazole method. [Z. Dische and E. Borenfreund, J. Biol. Chem. 192; 583, (1951) ].

The initial activity of the membrane complex was $8.3 \times 10^{-6}$ unit. The membrane complex was then washed with 1.5 liters of water and stored in 100 cc. of water at 4°C. for 17 hours before the second run. The second run showed a slight increase in activity which was probably due to an increase in reaction temperature from 60° to 65°C. in this run. An enzyme activity of $9.8 \times 10^{-6}$ unit was obtained. The membrane complex was then washed with another 1.5 liters of water and used in a third run at 60°C. The enzyme activity obtained was $8.7 \times 10^{-6}$ unit. By the third run, the membrane complex had been at 60°C. for more then six hours. These results demonstrate the stability and reuseability of the membrane complex.

It will be appreciated that while the foregoing disclosure relaates to only preferred embodiments of the invention for preparing active insoluble protein-enzyme complexes, numerous modifications or alterations may be made by those skilled in the art without departing from the spirit and scope of the invention as set forth in the appended claims.

What is claimed and intended to be secured by Letters Patent of the United States is:

1. An enzymatically active membrane prepared by a process comprising:

swelling a membrane formed from a protein selected from the group consisting of collagen, zein, casein, ovalbumin, wheat gluten, fibrinogen, myosin and mucoprotein, or a polypeptide selected from the group consisting of polyglutamate, polyaspartate, polyphenylalanine, polytyrosine and copolymer of leucine and p-amino phenylalanine to its maximum capacity;

soaking said swollen membrane in a enxyme-containing solution at a temperature of 4°–20°C for a period of 10 hours to 2 days at a pH between the isoelectric points of the enzyme and the polypeptide or protein membrane, thereby bonding said enzyme directly to said protein polypeptide of said membrane by the accumlative effects of van der Waals interactions, hydrogen bonding and salt linkages;

and thereafter drying said enzyme membrane complex.

2. The membrane of claim 1, wherein the dry thickness of said membrane is from 0.005 mm. to 0.1 mm.

3. The membrane of claim 1, wherein said enzyme is selected from the group consisting of oxidoreductases, transferases, hydrolases, isomerases, and compatible mixtures thereof.

4. The membrane of claim 1, wherein said enzyme is selected from the group consisting of lysozyme, urease, amylase, invertase, cellulase, glucose isomerases, and compatible mixtures thereof.

5. The membrane of claim 1, wherein said protein membrane is collagen or zein.

6. The membrane of claim 2, wherein said protein membrane is collagen or zein.

7. The membrane of claim 6, wherein said enzyme is selected from the group consisting of oxidoreductases, transferases, hydrolases, isomerases, and compatible mixtures thereof.

8. The membrane of claim 6, wherein said enzyme is selected from the group consisting of lysozyme urease, amylase, invertase, cellulase, glucose isomerase, and compatible mixtures thereof.

9. The membrane of claim 8, which is layered on a self-supporting base.

10. The membrane of claim 9, wherein said self-supporting base is cellulose acetate.

* * * * *

UNITED STATES PATENT AND TRADEMARK OFFICE
CERTIFICATE OF CORRECTION

PATENT NO. : 3,977,941

DATED : August 31,1976

INVENTOR(S) :

It is certified that error appears in the above-identified patent and that said Letters Patent are hereby corrected as shown below:

Column 1, line 55, delete "absorption" and insert --adsorption--.

Column 2, line 11, delete "carbonhydrates" and insert --carbohydrates--.

Column 2, line 29, delete "aan" and insert --an--.

Column 2, line 56, delete "poypep-" and insert --polypep- --.

Column 3, line 6, delete "example" and insert --examples--.

Column 3, line 12, delete "phenylanaline" and insert --phenylalanine--.

Column 3, line 52, delete "anzymes" and insert --enzymes--.

Column 4, line 28, delete "Since" and insert --Suitable--.

Column 4, line 46, delete "enxyme" and insert --enzyme--.

Column 4, line 50, delete "enzyne" and insert --enzyme--.

Column 4, line 57, delete "enxymes" and insert --enzymes--.

Column 5, line 20, delete "monoethly" and insert --monoethyl--.

Column 5, line 51, delete "celluloses" and insert --cellulases--.

Column 5, line 65, delete "lysozyne" and insert --lysozyme--.

UNITED STATES PATENT AND TRADEMARK OFFICE

CERTIFICATE OF CORRECTION

PATENT NO. : 3,977,941

DATED : August 31,1976

INVENTOR(S) : [illegible]

It is certified that error appears in the above–identified patent and that said Letters Patent are hereby corrected as shown below:

Column 6, line 28, delete "enxyme" and insert --enzyme--.

Column 6, line 34, delete "if" and insert --is--.

Column 6, line 55, delete "washing" and insert --wishing--.

Column 7, line 12, delete "Once" and insert --One--.

Column 7, line 17, delete "storated" and insert --stored--.

Column 8, line 42, delete "unrease" and insert --urease--.

Column 12, line 2, delete "relaates" and insert --relates--.

Column 12, line 20, delete "enxyme" and insert --enzyme--.

Column 12, line 25, after "protein" insert --or--.

Column 12, Claim 5, line 42, delete "membrane".

Column 12, Claim 6, line 44, delete "membrane".

Signed and Sealed this

*Thirty-first* Day of *January 1978*

[SEAL]

*Attest:*

RUTH C. MASON
*Attesting Officer*

LUTRELLE F. PARKER
*Acting Commissioner of Patents and Trademarks*